(12) United States Patent
Tinnin

(10) Patent No.: US 6,877,984 B2
(45) Date of Patent: Apr. 12, 2005

(54) DEVICE AND METHOD FOR CLEANING AND DETECTING FRACTURES IN FILES

(76) Inventor: James M. Tinnin, 1831 Green Acres Rd., Fayetteville, AR (US) 72703

( * ) Notice: Subject to any disclaimer, the term of this patent is extended or adjusted under 35 U.S.C. 154(b) by 82 days.

(21) Appl. No.: 10/097,788

(22) Filed: Mar. 13, 2002

(65) Prior Publication Data

US 2003/0186188 A1 Oct. 2, 2003

(51) Int. Cl.[7] ............................. A61C 5/02; A61B 19/02
(52) U.S. Cl. ...................... 433/102; 206/63.5; 206/366
(58) Field of Search .................................. 433/102, 141, 433/229; 206/63.5 R, 366 R, 368, 369

(56) References Cited

U.S. PATENT DOCUMENTS

| | | | |
|---|---|---|---|
| 4,058,215 A | * | 11/1977 | Marchbank .................. 206/574 |
| 4,191,291 A | | 3/1980 | Brown |
| 4,232,784 A | | 11/1980 | Hesselgren |
| 4,503,972 A | | 3/1985 | Nelligan et al. |
| 4,936,449 A | | 6/1990 | Conard et al. |
| 4,976,615 A | | 12/1990 | Kravitz |
| 5,743,734 A | | 4/1998 | Heath et al. |
| 5,967,778 A | | 10/1999 | Riitano |
| 6,036,490 A | * | 3/2000 | Johnsen et al. .............. 433/102 |

* cited by examiner

*Primary Examiner*—John J Wilson
(74) *Attorney, Agent, or Firm*—Boyd D. Cox

(57) ABSTRACT

A device for cleaning endodontic files and indicating flaws in endodontic files comprises a foam core contained in a housing and a covering overlaying the core through which a file is inserted into the device. A method for cleaning endodontic files using the device comprises the steps of inserting a file into the device and withdrawing the file. A method for detecting flaws in a file, includes the steps for cleaning the file and then examining the file for debris from the endodontic procedure adhering to the file which indicates the presence and location of damage to the file.

19 Claims, 3 Drawing Sheets

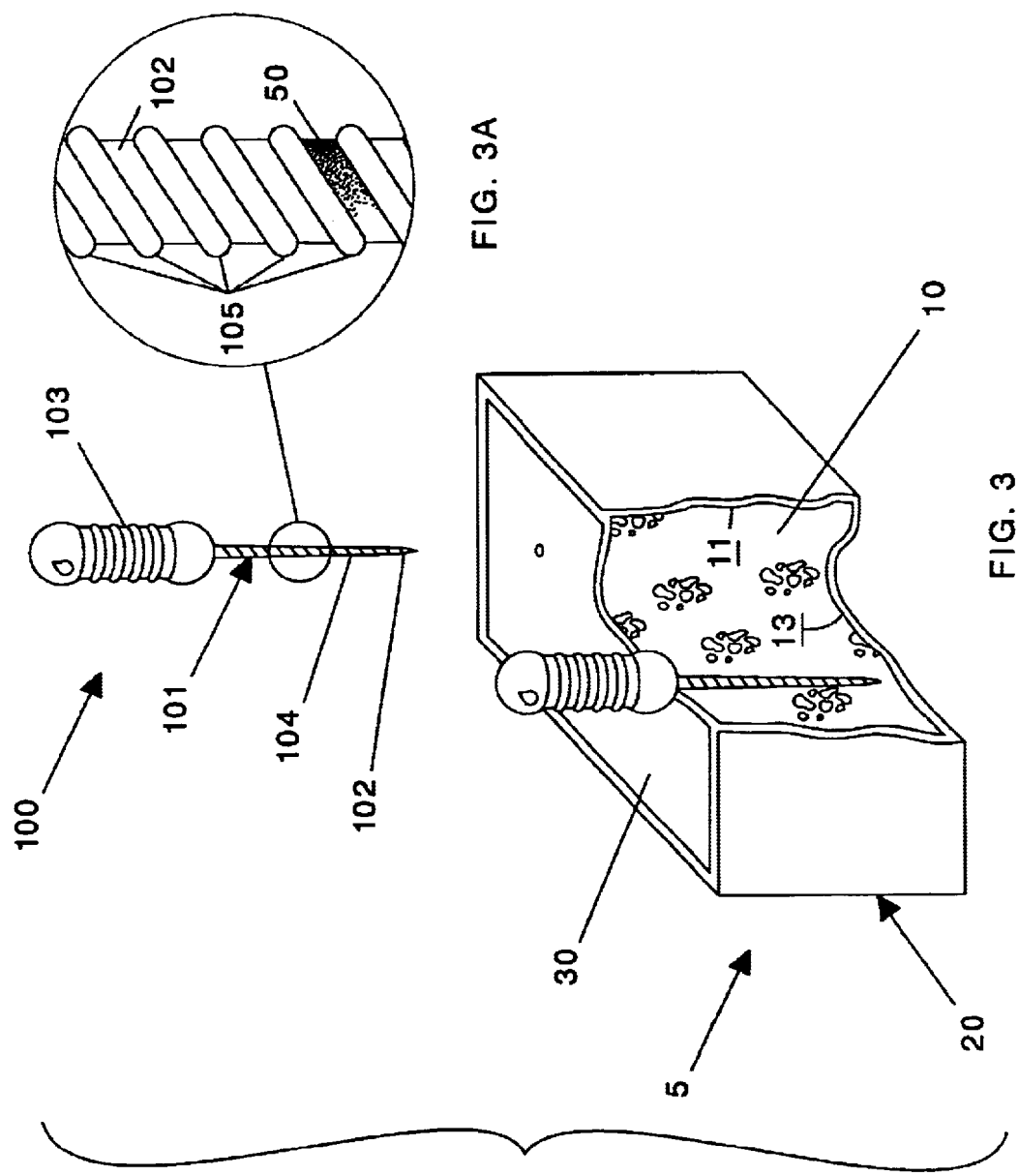

DEVICE AND METHOD FOR CLEANING AND DETECTING FRACTURES IN FILES

BACKGROUND

The present invention is directed to a device and method for cleaning endodontic files and a device for indicating flaws such as stress fractures and deformations in endodontic files. The invention also includes a method for detecting flaws in endodontic files.

An endodontic file, also known as a reamer, is a tool used to perform endodontic procedures. In an endodontic procedure, such as a root canal, the tissue in the pulp canals of the tooth is broken up with an endodontic file. The file is also used to mechanically clean and shape resultant tissue debris which includes pulp tissue and dentin from the tooth. Additionally, the file removes the tissue debris from the tooth during the endodontic procedure. The endodontic file can be manually manipulated during use or it can be attached to and rotated by a motorized drill.

An endodontic file generally comprises a shaft with flutes along its length. Because of the file's design and function, the tissue debris that has been loosened from the tooth can accumulate on the file during use, such that the flutes become clogged with the tissue debris. The accumulation of such debris on a file can cause deformation of the flutes which can lead to stress fractures and breaks in the file. Consequently, it is desirable to remove the debris from the file and flutes at regular intervals during the course of an endodontic procedure. Regular cleaning of the file during use reduces the risk of file damage and allows for an unimpeded visual inspection of the file.

Typically, to clean a file during or after an endodontic procedure the file is wiped down to remove as much tissue debris as possible from the flutes. However, such a cleaning method is problematic since the flutes on the file make it difficult to wipe the debris from the file. Likewise, rinsing the file is ineffective in removing all of the debris that lodges in and around the flutes. Tissue remaining on the file can inhibit the user from visually detecting deformations in the file. Unchecked accumulation of debris on the flutes can cause deformations to form in the file which can create stress fractures and eventually cause file breakage. Failure to promptly detect such flaws can prompt continued use of the file and its eventual failure during use.

After an endodontic procedure, a file is typically cleaned to remove the tissue debris and then sterilized to prepare it for subsequent use with another patient or procedure. Debris that has not been completely removed from an endodontic file during such cleaning is not generally removed by standard sterilization procedures, such as autoclaving and ultrasonic cleaning. Consequently, tissue debris can remain on the file during and after sterilization. Using a file with tissue debris still adhering can compromise the requisite health standards for an endodontic procedure by increasing the risk of infection to the patient. Therefore, not only does using a file with debris clogged in its flutes further increase the possibility of file failure, but it can also present a health hazard.

Endodontic files are required to endure sustained pressure during use, despite their flexibility. Therefore, the files are designed and manufactured for strength and durability. However, when weakened due to repeated use, a file has the tendency to deform and develop stress fractures. Deformations and stress fractures in a file can lead to an endodontic file breaking apart. Since the files are used in a patient's tooth, a file breaking during use can be especially hazardous. When a file breaks apart in a tooth, the procedure must be halted while the broken file pieces are retrieved from the patient's mouth. This can be frustrating and time-consuming. As a result, file breakage not only creates a safety hazard and potential liability, it can unduly prolong the endodontic procedure. Stress fractures in endodontic files are generally undetectable to the naked eye. Methods of detecting stress fractures including X-ray techniques have been developed, but due to cost and time constraints, such techniques are impractical to use in routine clinical procedures. Stress fractures, along with deformations, can be especially difficult to detect when the file has an accumulation of tissue debris in and around the flutes.

As a precautionary measure to minimize file breakage, a user generally replaces the file after a recommended period of use. By regular replacement according to a manufacturer's recommended usage, file breakage can be minimized, but the life of the file is foreshortened resulting in increased cost to the user. Even if the file is discarded as recommended by the manufacturer, stress fractures, file deformation and breakage can still occur due to cyclic fatigue.

Regardless of a file's foreshortened life, such recommended time periods generally would not apply to files having manufacturing defects. Such defects can allow file deformations and stress fractures to form prematurely resulting in unexpected failure and file breakage, sometimes while the file is in use.

Therefore, there is a need for a device that can readily indicate flaws in an endodontic file while using the file in an endodontic procedure. There is also a need for a method for readily detecting flaws in endodontic files. The need also exists for a device and method to effectively clean tissue debris from an endodontic file, especially around the flutes, during and after an endodontic procedure in order to reduce the possibility of file damage, including breakage, and to lower the risk of patient infection resulting from an unclean file.

SUMMARY

The present invention is a device for cleaning and a device for indicating flaws in an endodontic file in addition to a method for cleaning and a method for detecting flaws in an endodontic file. The device comprises a foam core with a housing and a covering. The housing encloses the sides and bottom of the foam core. The covering overlays the top surface of the foam core. Layers of fabric that comprise the covering are penetrable by a file.

The method of cleaning the endodontic file comprises the steps of inserting the file into the device by forcing the file through the covering and into the foam core, then withdrawing the file from the device. The method of detecting flaws comprises the steps for cleaning the file and further comprises examining the file for the presence of debris removed from the tooth that remains adhered to the file after the steps for cleaning have been performed. The presence of such tissue debris adhering to the file's bit after the file has been cleaned using the device indicates the likelihood of file damage. This debris has a tendency to accumulate and remain on an area of the file proximate the location of the file damage, generally manifesting as deformations, stress fractures or breaks in the endodontic file.

It is an object of the present invention to provide a device for cleaning the tissue debris from an endodontic file.

It is a further object of the present invention to provide a device for indicating flaws in an endodontic file.

It is a further object of the present invention to provide a device for indicating deformations in an endodontic file.

It is a further object of the present invention to provide a device for indicating stress fractures in an endodontic file.

It is an object of the present invention to provide a method for readily detecting flaws in an endodontic file while using the file in an endodontic procedure.

It is an object of the present invention to provide a means to reduce the risk of breaking an endodontic file during use.

It is an object of the present invention to increase the safety of performing a root canal in a dental patient.

It is an object of the present invention to provide a device that can effectively remove tissue debris from an endodontic file and alternatively indicate the presence of flaws in the file.

It is an object of the present invention to provide a device and method for quickly locating occurring stress fractures and/or deformations in an endodontic file.

It is an object of the present invention to provide a means and device for locating stress fractures and/or deformations in a file during an endodontic procedure.

It is an object of the present invention to provide a device that readily cleans tissue debris from an endodontic file.

It is an object of the present invention to provide a device for removing the tissue debris from the flutes of an endodontic file.

It is an object of the present invention to provide a method for detecting a damaged endodontic file.

It is an object of the present invention to provide a device for indicating damage in an endodontic file.

BRIEF DESCRIPTION OF DRAWINGS

Reference is made to the accompanying drawings in which are shown illustrative embodiments of the invention and from which novel features and advantages will be apparent.

FIG. 3 is a partial cut-away view of the device of FIG. 1 showing endodontic files therewith.

FIG. 3A is a close-up of an endodontic file that has been inserted into and removed from the device of FIG. 1 and depicts the occurrence of a flaw on the file.

DETAILED DESCRIPTION

Figure 1:
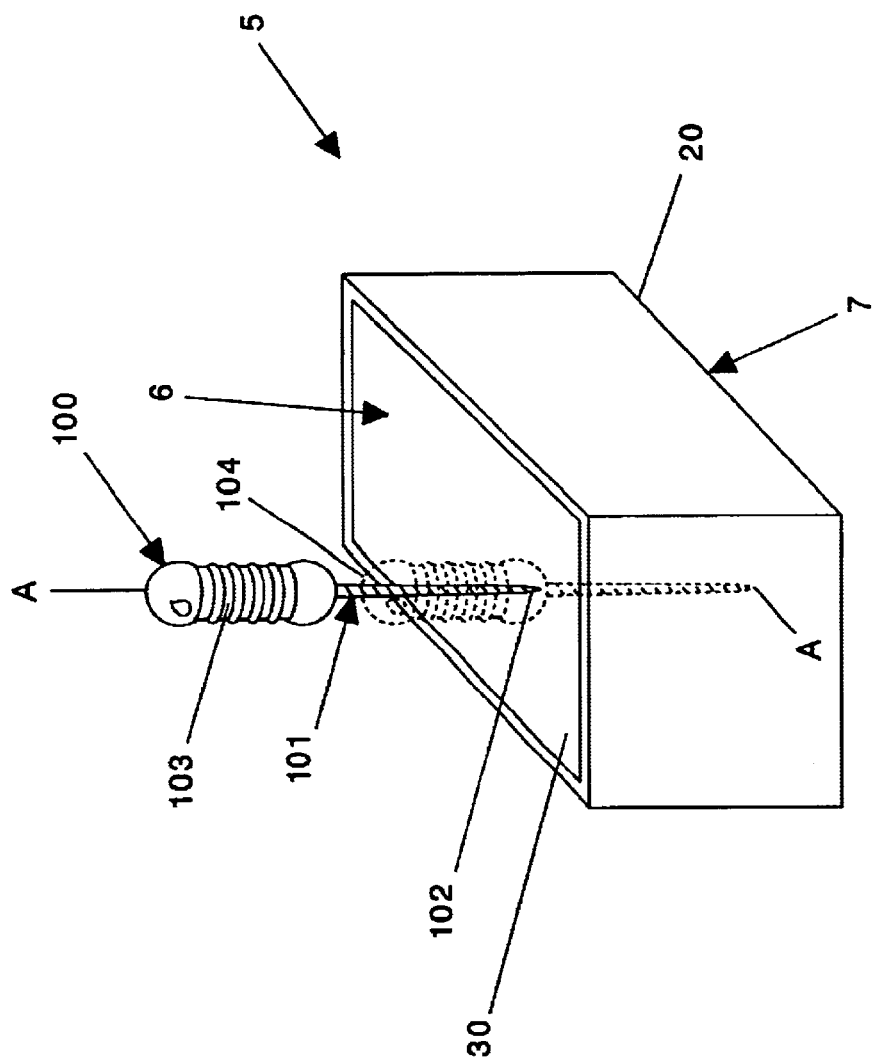
FIG. 1 is a perspective view of a preferred embodiment of the endodontic device of the present invention. A file is shown in solid lines to be poised for insertion into the device and another file is shown in dotted lines to be fully inserted into the device.

An endodontic file or reamer is used to loosen and remove tissue debris from the pulp canals in the root of a tooth. The tissue is loosened and removed when performing endodontic procedures, including root canals. An endodontic file 100 intended for manual manipulation is shown by FIG. 1. It should be appreciated that the file shown herein is illustrative only and an endodontic file adapted for use with a motorized drill could be used with the present invention, as well.

The endodontic file 100 in FIG. 1 comprises a handle 103 and a bit 101 comprising a tip 102 and an elongated body 104 having flutes 105 along a length of the bit 101. The elongated body 104 extends along a longitudinal axis A.

Figure 2:
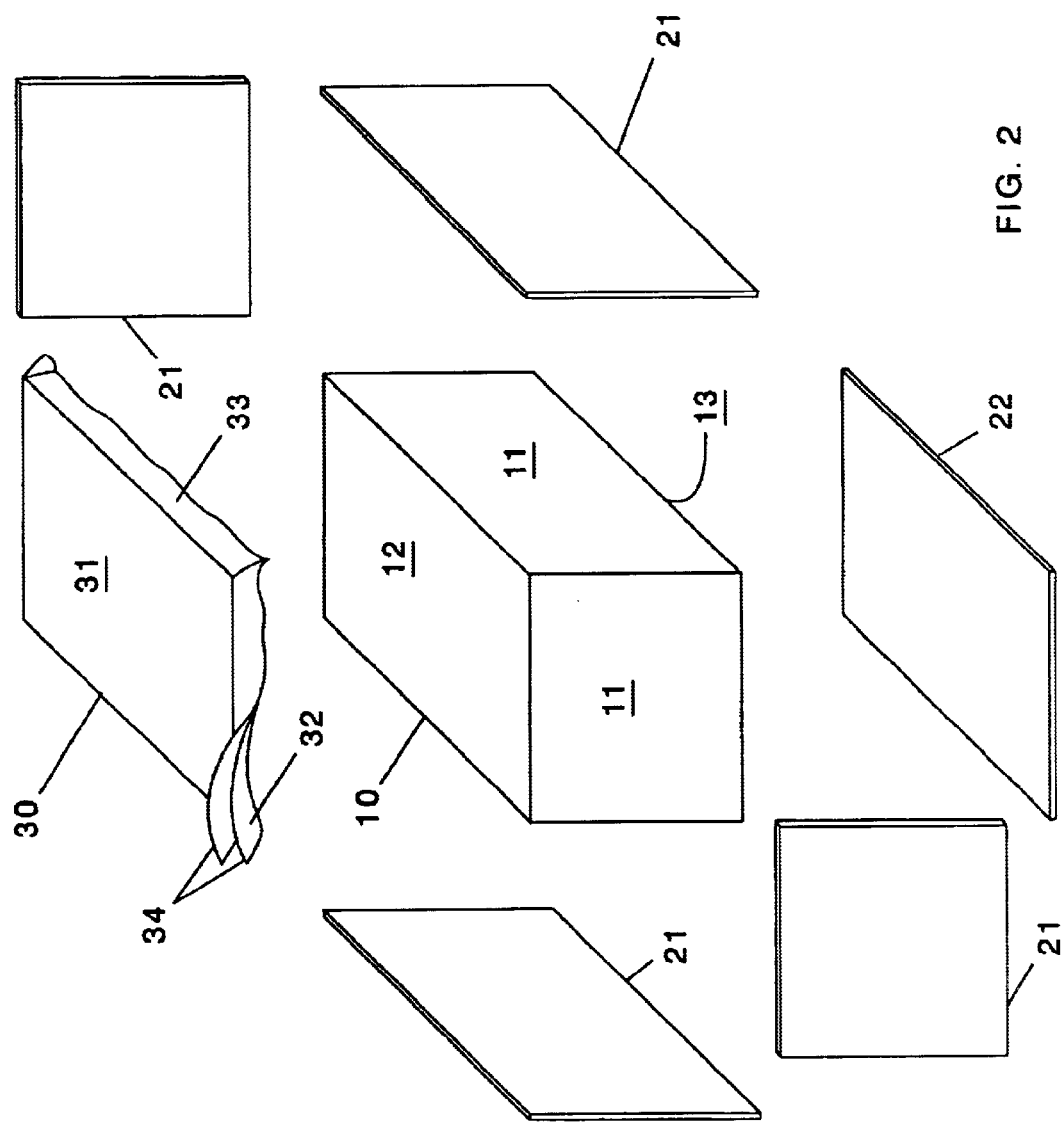
FIG. 2 is an exploded perspective of the endodontic device of FIG. 1.

Referring to FIGS. 1 and 2, there is shown a preferred embodiment of the device 5 of the present invention. The device 5 has upper 6 and lower 7 sides and is comprised by a foam core 10, a housing 20, and a covering 30.

The foam core 10 has a plurality of side surfaces. The plurality of side surfaces includes outer side surfaces 11, a top surface 12 and a bottom surface 13. The housing 20 comprises a plurality of walls which includes side walls 21 and a bottom wall 22. The housing's respective side walls 21 and bottom wall 22 correspond to the outer side surfaces 11 and the bottom surface 13 of the foam core 10.

The covering 30 is characterized as having an outer surface 31 and an inner surface 32. The covering 30 preferably includes a plurality of pliable sheets in which each sheet is a layer 34 of fabric.

In a preferred embodiment, the foam core 10 has a rectangular shape with an approximate size of 1"×2"×3". However, the size and shape of the device 5 can vary, as desired. The housing 20 is sized to surround the outer side surfaces 11 and bottom surface 13 of the foam core 10 with the side 21 and bottom 22 walls of the housing 20 generally conforming to the shape and size of the respective side 11 and bottom 12 surfaces of the foam core 10.

The foam core 10 comprises polystyrene cellular foam. The housing is made of a stiff material that is relatively resistant to file penetration during normal use, such as cardboard. The fabric of the covering is pliable and is penetrable by a file. It comprises a blend of rayon and polyester.

The polystyrene cellular foam is commercially manufactured under the name of Beinfang foamboard and is available from Hunt-Bienfang Products in Statesville, N.C. The fabric comprising the covering is commercially available under the trade name "Nu Gauze" General Use Sponges which are manufactured by Johnson & Johnson Medical Division of Ethicon, Inc. in Arlington, Tex. Although it is preferable to use cardboard for the housing 20, plastic or other suitable substitutes could be used instead for the housing 20. Likewise, other suitable substitutes could be used for the foam and fabric described above.

Both the covering 30 and foam core 10 are penetrated by the file 100 during use. The core 10 and covering 30 cooperate to clean the file 100 by loosening and removing tissue debris from the file's bit 101 as the file 100 moves into and out of the device 5.

In a preferred use, the covering 30 provides initial and final cleaning of the bit 101. The tissue debris 50 on an undamaged file is displaced and deposited primarily in the covering 30 when the file 100 is inserted into the device 5. After penetrating the covering 30, the file 100 enters the foam core 10 where the debris 50 is further loosened and removed from the flutes 105 and the rest of the file's bit 101. In addition, the covering 30 protects the top surface 12 of the foam core 10 from external damage.

Referring to FIGS. 3 and 3A, tissue debris 50 will adhere to and remain on a file after it has been inserted into and removed from the device 5 when flaws, including stress fractures and/or deformations, are present in the file. The tooth debris 50 tends to accumulate on the area of the file proximate the location of a flaw in the file 100. Consequently, the accumulation of tissue debris 50 on the bit 101 after the file's insertion into and removal from the device 5 indicates the probability that the file 100 has been damaged.

The housing 20 acts as a barrier. It deters the tip 102 of the file 100 from protruding out of the device 5 as the file 100 is inserted therein. By keeping the file 100 within the confines of the device 5, the risk of injury to a user when he or she is using the device 5 is decreased. Since the housing 20 covers the sides 11 and bottom 13 surfaces of the foam core 10, the housing 20 protects the foam core 10 from external damage.

In a preferred embodiment of the device 5 as shown in FIGS. 1 and 2, the foam core 10 is positioned within the confines of the housing 20 such that the bottom surface 13 of the foam core 10 is adjacent to the bottom wall 22 of the housing 20. Each outer side surface 11 of the foam core 10 is adjacent to a corresponding side wall 21 of the housing 20.

The covering 30 is on the upper side 6 of the device 5 and overlays the top surface 12 of the foam core 10. The inner surface 32 of the covering 30 is adjacent to the top surface 12 of the foam core 10. Along with the housing 20, the outer surface 31 of the covering 30 forms the exterior of the device 5.

Forming the housing 20, the side walls 21 are attached to each other and attached to the bottom wall 22. The covering 30 is comprised of two layers 34 of fabric that extend over the top surface 12 of the foam core 10. A fewer or greater number of layers can be used, if desired.

In a preferred embodiment of FIG. 2, the housing 20 covers the outer side surfaces 11 and the bottom surface 13 of the foam core 10. Each side wall 21 covers a respective outer side surface 11 of the foam core 10. The covering 30 is larger than the top surface 12 and edges 33 around the perimeter of the covering 30 overlap onto the outer side surfaces 11 of the foam core 10. The side walls 21 of the housing 20 overlay the portion of the edges 33 against the outer side surfaces 11 to secure the covering 30 in place on the foam core 10. The covering 30 can also be held in place by other means, such as by the thumb and fingers of the user, if desired.

In use, a endodontic file 100 is inserted into the device 5. Preferably, the file is inserted into the device 5 a distance that is at least the approximate length along the file's bit 101 that the flutes 105 extend. The file 100 is withdrawn from the device and examined for the presence of tissue debris 50 that may be adhering to the bit 101 on and around the flutes 105. Preferably, the file 100 is rotated during insertion and removal from the device 5.

To clean an endodontic file 100 with the device 5 of the present invention, the file 100 is positioned on the upper side 6 of the device 5 with the tip 102 pointed toward the covering 30 as shown in FIG. 1. The file 100 is then pressed into the device 5 as the file 100 is rotated. As the file 100 is pressed into the device 5, the tip 102 passes through the covering 30 and enters into the foam core 10. The body 104 of the file 100 follows the tip 102 through the covering 30 and into the foam core 10 of the device 5. Preferably, the file 100 is pressed until fully inserted, as with the inserted file 100 shown in FIG. 3. When the file 100 is fully inserted, the flutes 105 on the bit 101 are substantially contained within the device 5. If, during insertion, the file's tip 102 contacts the housing 20 before the bit 101 is fully inserted into the device 5, the file 100 should be completely withdrawn from the device 5 and reinserted until the bit 101 is fully inserted. The file 100 is withdrawn from the device 5 in an order opposite to that of its insertion. Upon withdrawal, the bit 101 exits the foam core 10, and finally exits the covering 30.

As the file 100 passes through the device 5, tissue debris 50 that has accumulated on the file 100 from the endodontic procedure is loosened and removed from the file 100. This debris 50 is primarily deposited on the covering 30, but can also be retained by the foam core 10. If unflawed or undamaged, the file 100 emerges from the device 5 devoid of debris.

However, in the event that there is a flaw in the file 100, the tooth debris 50 that has been displaced from the patient's tooth adheres to the bit 101 after the file 100 has been fully inserted into and withdrawn from the device. The tissue debris 50 remains dispersed on the outer surface of the file 100. This debris 50 tends to accumulate on the bit 101 in areas proximate any stress fractures and/or deformations occurring in the bit 101.

A visual inspection of the flutes 105 and bit 101 to discern the presence or absence of debris 50 on the file 100 is conducted immediately after cleaning. The inspection can be done with the naked eye. If the inspection of the file 100 reveals the presence of debris 50 on the bit 101, as shown in FIG. 3A, the potential for a significant flaw or flaws in that file exists and the file should be discarded. The absence of debris on the file indicates the likelihood that no significant flaw(s) have formed in the file and, therefore, suggests no contraindication to its continued use.

A preferred method of cleaning an endodontic file comprises the steps of inserting the bit of the file into the device and removing the file from the device. The steps can be repeated as desired. The file can be rotated within the device after insertion. The file may also be rotated during entry into the device and/or during removal from the device. The rotation is clockwise about the longitudinal axis of the file's bit.

This preferred method of cleaning an endodontic file further comprises the steps of providing a device for cleaning the endodontic file; positioning the file proximate the upper side of the device with the tip of the file's bit pointing toward the covering; inserting the file into the device while rotating the file in a clockwise direction about the longitudinal axis of the bit; and removing the file from the device while rotating the file in a clockwise direction about the longitudinal axis of the bit.

The step of inserting the file into the device further comprises the steps of inserting the tip of the bit into the covering; pressing the tip through the covering and into the foam core; and pressing the body of the bit through the covering and into the foam core until the file is fully inserted, wherein the flutes are substantially contained by the device and the handle of the file is proximate the upper side of the device. The step of removing the file from the device further comprises the steps of withdrawing the body from the foam core and back through the covering; withdrawing the tip from the foam core; and withdrawing the tip from the covering.

The method of detecting flaws in an endodontic file comprises the steps in the method for cleaning the file and further includes the step of examining the file for tissue debris adhering to the bit. This step is performed after removing the file from the device. The presence of tissue debris adhering to the bit indicates a strong possibility of stress fractures and/or deformations present in the file proximate the location of the debris on the bit. It should also be noted that foam particles from the foam core may also adhere to the bit and be an indication of the location of such stress fractures and/or deformations.

The device of the present invention enables a user to readily clean an endodontic file during its use in an endodontic procedure. The user inserts the file into the device and withdraws it to clean the debris from the file. With the debris removed from the file, a user is better able to inspect the flutes on the file for deformations or other damage to the file.

In addition to cleaning, the device can be used to detect flaws in a file and thereby gauge the useful life of the file. Tissue debris adhering to the file after cleaning indicates the presence and location of flaws in the file. When the presence of a flaw is indicated by the present invention, the damaged file can be readily identified and discarded.

Flaws such as deformations and stress fractures are precursors to file breakage. Since these flaws can be detected promptly using the present invention, the possibility of breaking a file in a patient's mouth during a procedure can be reduced. This increases the safety of an endodontic procedure. Also, by avoiding file breakage, the time required to perform a procedure is reduced since the need to retrieve a broken file is eliminated.

In an alternate embodiment, the walls of the housing are discrete elements that are not attached to each other. Instead, each side wall and the bottom wall attaches directly to the corresponding surface of the foam core.

In another alternate embodiment, the covering of the device is eliminated such that the file initially enters the foam core when inserted into the device. The top surface of the foam core forms the upper side of the device's exterior.

Although the present invention has been described in considerable detail with reference to certain preferred versions thereof, other versions are possible. Therefore, the spirit and scope of the appended claims should not be limited to the description of the preferred versions contained herein.

What is claimed is:

1. A device for cleaning an endodontic file used in endodontic procedures, wherein the file comprises a bit having a longitudinal axis and flutes, the device comprising:
   a foam core;
   a housing at least partially surrounding said foam core;
   a covering disposed on said foam core, wherein said covering is penetrable by the file and said covering comprises at least one pliable sheet of fabric; and
   said foam core comprises polystyrene cellular foam and said fabric comprises a blend of rayon and polyester;
   wherein to clean the file, the file is inserted through said covering and into said foam core, and the file is withdrawn from the device.

2. The device of claim 1, wherein said at least one pliable sheet comprises a plurality of pliable sheets.

3. The device of claim 1, wherein to indicate a flaw in a file, the file is inserted through the covering into the foam core, the file is removed from the device, and debris from the endodontic procedure adhering to the file indicates locations of the flaws on the file.

4. The device of claim 1, wherein said foam core includes a top surface, a bottom surface and outer side surfaces, said housing having a bottom wall and side walls, wherein each of said side walls of the housing corresponds to a respective one of said outer side surfaces of the foam core, and the bottom wall of the housing corresponds to the bottom surface of the foam core.

5. The device of claim 4, further comprising a covering having an edge extending around a perimeter thereof, said covering is disposed adjacent to the top surface of the foam core and at least a portion of the edge of said covering is disposed adjacent to the side walls of the foam core such that the portion of the edge is secured between the side surfaces of the foam core and the side walls of the housing.

6. The device of claim 1, wherein to indicate a flaw, the file is cleaned by insertion into the device such that the flutes are extended through the covering and into the foam core, then the file is removed from the device such that the flutes are withdrawn from the foam core and the covering, and the file is examined for a presence or absence of debris from the endodontic procedure adhering to the bit, such that the presence of debris indicates a flaw proximate the debris on the file and the absence of debris indicates the file is not flawed; and when debris is present on the endodontic file after cleaning, the file is discarded.

7. A method for detecting flaws in an endodontic file for use in endodontic procedures, wherein the file comprises a bit having flutes, an attached end, an unattached end and a longitudinal axis, said bit further comprises a tip at said unattached end and an elongated body extending between the tip and the attached end, the method for detecting flaws comprises:
   providing a device having upper and lower sides, said device comprises a foam core, a housing and a covering, wherein said foam core is comprised of polystyrene cellular foam, said foam core further includes a top surface, a bottom surface and outer side surfaces, said housing has a bottom wall and side walls, said covering has outer and inner surfaces and comprises at least one layer of fabric, the fabric comprises rayon and polyester, said housing substantially surrounds said outer side surfaces and bottom surface of said foam core, said covering overlays the top surface of said foam core;
   positioning the file proximate the upper side of the device with the tip of the file toward the covering;
   inserting the file into the device, wherein inserting the file into the device further comprises the steps of:
      (a) inserting the tip of the bit into the covering;
      (b) pressing the tip through the covering and into the foam core; and
      (c) pressing the body of the bit through the covering;
      (d) pressing the body into the foam core until the flutes of the file are contained within the device;
   removing the file from the device, wherein removing the file from the device further comprises the steps of:
      (a) withdrawing the body of the bit from the foam core and through the covering while simultaneously withdrawing the tip from the foam core; and
      (b) withdrawing the tip from the covering;
   examining the file for the presence or absence of debris from the endodontic procedure adhered to the file, wherein the presence of debris indicates a flaw proximate a location of the debris on the file and the absence of debris indicates the file is not flawed; and
   discarding the file when the presence of debris is detected on the file.

8. The method of claim 7, wherein the file is rotated in a clockwise direction about the longitudinal axis of the bit while at least a portion of the file is within the device.

9. A device for indicating flaws in an endodontic file used in endodontic procedures, wherein the file comprises a bit having a longitudinal axis and flutes, the device comprising:
   a foam core;
   a housing at least partially surrounding said foam core;
   a covering disposed on said foam core, wherein said covering is penetrable by the file and said covering comprises at least one pliable sheet of fabric; and
   said foam core comprises polystyrene cellular foam; and
   said fabric comprises a blend of rayon and polyester;
   wherein to indicate a flaw, the file is cleaned by insertion into the device such that the flutes are extended through the covering and into the foam core, then the file is removed from the device such that the flutes are withdrawn from the foam core and the covering, and the file is examined for a presence or absence of debris from the endodontic procedure adhering to the bit such that the presence of debris indicates a flaw proximate the debris on the file and the absence of debris indicates the file is not flawed; and wherein when debris is present on the endodontic file after cleaning, the file is discarded.

10. The device of claim 9, wherein said at least one pliable sheet comprises a plurality of sheets.

11. A method for detecting flaws in a file, wherein the file comprises a bit having flutes, a longitudinal axis, an unattached end, an elongated body, and a tip at said unattached end, the method for detecting flaws comprises:

providing a device with upper and lower sides, said device further comprises a foam core, a housing at least partially surrounding the foam core and a covering adjacent to the foam core;

positioning the file proximate the upper side of the device with the tip of the file toward the covering;

inserting the file into the device;

removing the file from the device; and examining the file for a presence or absence of debris adhered to the file, wherein the presence of debris indicates a flaw proximate a location of the debris on the file and the absence of debris indicates the file is not flawed; and discarding the file when the presence of debris is detected on the file.

12. The method of claim 11, wherein the file is rotated in a clockwise direction about the longitudinal axis of the bit while at least a portion of the file is within the device.

13. The method of claim 11, wherein inserting the file into the device further comprises the steps of:

inserting the tip of the bit into the covering;

pressing the tip through the covering and into the foam core; and pressing the elongated body through the covering and into the foam core; removing the file from the device further comprises the steps of:

withdrawing the elongated body from the foam core and through the covering;

withdrawing the tip from the foam core; and withdrawing the tip from the covering.

14. The method of claim 13, further comprising the step of:

rotating the file in a clockwise direction about the longitudinal axis of the bit while inserting the file into the device.

15. The method of claim 13, further comprising the step of:

rotating the file in a clockwise direction about the longitudinal axis of the bit after inserting the file into the device.

16. The method of claim 13, further comprising the step of:

rotating the file in a clockwise direction about the longitudinal axis of the bit while removing the file from the device.

17. The method of claim 11, wherein said foam core comprises polystyrene cellular foam.

18. The method of claim 11, wherein said covering comprises at least one layer of fabric.

19. The method of claim 18, wherein said fabric comprises rayon and polyester.

* * * * *